US012751765B2

(12) United States Patent
Genovese et al.

(10) Patent No.: US 12,751,765 B2
(45) Date of Patent: Oct. 6, 2026

(54) VALVE LEAFLET RESECTION DEVICE

(71) Applicant: Medtronic, Inc., Minneapolis, MN (US)

(72) Inventors: Matthew Genovese, Windsor, CA (US); Jonathan Primeaux, Santa Rosa, CA (US); William Chang, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 153 days.

(21) Appl. No.: 18/695,329

(22) PCT Filed: Sep. 29, 2022

(86) PCT No.: PCT/IB2022/059313
§ 371 (c)(1),
(2) Date: Mar. 25, 2024

(87) PCT Pub. No.: WO2023/053068
PCT Pub. Date: Apr. 6, 2023

(65) Prior Publication Data

US 2024/0398472 A1 Dec. 5, 2024

Related U.S. Application Data

(60) Provisional application No. 63/251,509, filed on Oct. 1, 2021.

(51) Int. Cl.
*A61B 18/14* (2006.01)
*A61B 17/22* (2006.01)
(Continued)

(52) U.S. Cl.
CPC .................... *A61B 18/1492* (2013.01); *A61B 2017/22069* (2013.01); *A61B 17/221* (2013.01);
(Continued)

(58) Field of Classification Search
CPC ................ A61B 17/221; A61B 17/295; A61B 17/320016; A61B 18/1492;
(Continued)

(56) References Cited

U.S. PATENT DOCUMENTS 5,584,803 A * 12/1996 Stevens ................ A61F 2/2433 604/6.16
2002/0013571 A1* 1/2002 Goldfarb ................ A61B 50/30 606/1
(Continued)

OTHER PUBLICATIONS

International Search Report and Written Opinion, International Application No. PCT/IB2022/059313, mailed Jan. 12, 2023, 14 pages.

*Primary Examiner* — Tigist S Demie
(74) *Attorney, Agent, or Firm* — Medler Ferro Woodhouse & Mills PLLC

(57) ABSTRACT

A valve leaflet resection device includes a catheter (110), an electrode assembly (140) slidably disposed within the catheter and deployable from the catheter and configured to remove a portion of a leaflet of a heart valve, a leaflet retainer (130) slidably disposed within the catheter and deployable from the catheter, the leaflet retainer configured to grasp a leaflet of a heart valve, and a capture basket (120) configured to capture a resected portion of the leaflet of the heart valve upon retraction of the leaflet retainer.

20 Claims, 16 Drawing Sheets

(51) Int. Cl.
*A61B 17/221* (2006.01)
*A61B 17/295* (2006.01)
*A61B 18/00* (2006.01)

(52) U.S. Cl.
CPC ... *A61B 17/295* (2013.01); *A61B 2018/00369* (2013.01); *A61B 2018/00601* (2013.01); *A61B 2018/1422* (2013.01); *A61B 2018/1475* (2013.01)

(58) Field of Classification Search
CPC ........... A61B 2017/00243; A61B 2017/00287; A61B 2017/00783; A61B 2017/22069; A61B 2017/22097; A61B 2017/2215; A61B 2018/00369; A61B 2018/00601; A61B 2018/1422; A61B 2018/1475
See application file for complete search history.

(56) References Cited

U.S. PATENT DOCUMENTS

| | | | | |
|---|---|---|---|---|
| 2008/0039881 | A1* | 2/2008 | Greenberg ............. | A61B 17/22 606/170 |
| 2012/0010699 | A1 | 1/2012 | Vesely | |
| 2013/0116715 | A1 | 5/2013 | Weber | |
| 2014/0018788 | A1* | 1/2014 | Engelman .......... | A61B 18/1492 606/33 |
| 2019/0298517 | A1 | 10/2019 | Sanchez et al. | |
| 2020/0146691 | A1 | 5/2020 | Rothstein et al. | |

* cited by examiner

VALVE LEAFLET RESECTION DEVICE

FIELD OF THE INVENTION

The present invention relates to a valve leaflet resection device.

BACKGROUND

Deployment of a second transcatheter heart valve prosthesis within a previously implanted surgical or transcatheter heart valve prosthesis is referred to as a valve-in-valve procedure. At a native aortic valve, coronary artery obstruction may occur when leaflets of the first implanted valve (or the native valve) are displaced towards the coronary ostia or sinotubular junction during deployment of the second transcatheter valve deployment, thus obstructing coronary blood flow.

SUMMARY

Aspects of the present application are directed to a valve leaflet resection device.

In a first example, the valve leaflet resection device includes a valve leaflet resection device includes a catheter, an electrode assembly slidably disposed within the catheter and deployable from the catheter and configured to remove a portion of a leaflet of a heart valve, a leaflet retainer slidably disposed within the catheter and deployable from the catheter, the leaflet retainer configured to grasp a leaflet of a heart valve, and a capture basket configured to capture a resected portion of the leaflet of the heart valve upon retraction of the leaflet retainer.

In a second example, in the valve leaflet resection device of the first example, the capture basket includes a radially compressed configuration and a radially expanded configuration.

In a third example, in the valve leaflet resection device of the first example or the second example, the capture basket is disposed co-axially around the leaflet retainer.

In a fourth example, in the valve leaflet resection device of any of the preceding examples, the capture basket is a tapered mesh tube having a distal end with a first dimension in the radially expanded configuration transverse to a central longitudinal axis of the catheter and a proximal end with a second dimension in the radially expanded configuration transverse to the central longitudinal axis, wherein the second dimension is smaller than the first dimension.

In a fifth example, in the valve leaflet resection device of any of the preceding examples, the capture basket further includes a wire or tube extending proximally to an actuator to translate the capture basked proximally and distally in and out of the catheter.

In a sixth example, in the valve leaflet resection device of any of the first through third examples, the capture basket is attached to a distal end of the catheter.

In a seventh example, in the valve leaflet resection device of any of the preceding examples, the leaflet retainer comprises a wire including a hook at a distal end thereof, wherein the wire is shape set to form the hook as the wire is distally advanced out of the catheter In an eighth example, in the valve leaflet resection device of the seventh example, the leaflet retainer further includes an electrode at the distal end thereof configured to pierce the leaflet to be resected.

In a ninth example, in the valve leaflet resection device of any one of the first through sixth examples, the leaflet retainer comprises a tube and a balloon slidably disposed within the tube, wherein the tube is configured to be advanced adjacent to a first side of the leaflet to be resected, the balloon in an uninflated state is configured to exit the tube and advance through the leaflet to a second side of the leaflet, and wherein the balloon is further configured to be inflated to an inflated state wherein the leaflet is captured between the balloon in the inflated state and the tube.

In a tenth example, in the valve leaflet resection device of any one of the first through sixth examples, the leaflet resection device comprises a tube and a wire having a shape set tip slidably disposed within the tube, wherein the tube is configured to be advanced adjacent to a first side of the leaflet to be resected, the wire in a straightened configuration is configured to exit the tube and advance through the leaflet to a second side of the leaflet, and wherein the shape set tip is configured to bend to its shape set to capture the leaflet between the shape set tip and the tube.

In an eleventh example, in the valve leaflet resection device of any one of the first through sixth examples, the leaflet retainer comprises a proximal balloon and a distal balloon, wherein the proximal balloon and the distal balloon are configured to be advanced adjacent to first side of the leaflet to be resected in an uninflated state, the distal balloon in the uninflated state is configured to exit be advanced through the leaflet to a second side of the leaflet, and wherein the proximal and distal balloons are further configured to be inflated to an inflated state such that the leaflet is captured between the proximal balloon and the distal balloon.

In a twelfth example, in the valve leaflet resection device of any one of the first through sixth examples, the leaflet retainer comprises a shape set wire configured to form a proximal radial bump and a distal radial bump in a shape set configuration, wherein the shape set wire is configured to be advanced adjacent to first side of the leaflet to be resected in a straightened configuration, the wire in the straightened configuration is configured to exit the tube and advance through the leaflet to a second side of the leaflet, and wherein the wire is configured to return to shape set configuration to capture the leaflet between the proximal radial bump on the first side of the leaflet and the distal radial bump on the second side of the leaflet.

In a thirteenth example, in the valve leaflet resection device of any one of the first through sixth examples, the leaflet retainer includes a shaft having an auger or helical coil at a distal end of the shaft, wherein the shaft is configured to be advanced through the leaflet to be resected such that a first portion of the auger or helical coil is on a first side of the leaflet and a second portion of the auger or helical coil is on a second side of the leaflet to grasp the leaflet.

In a fourteenth example, in the valve leaflet resection device of any one of the first through sixth examples, the leaflet retainer includes a shaft with a proximal retainer and a distal retainer disposed on the shaft, wherein the proximal and distal retainers include a radially compressed configuration when disposed within the catheter, wherein the catheter is configured to the advanced to a first side of the leaflet to be resected, the leaflet retainer is configured to be advanced from the catheter through the leaflet such that the distal retainer is on a second side of the leaflet and the proximal retainer is on the first side of the leaflet, and wherein the distal and proximal retainers are configured to radially expand to a radially expanded configuration when exiting the catheter such that the leaflet is captured between the proximal leaflet and the distal leaflet with each in the radially expanded configuration.

In a fifteenth example, in the valve leaflet resection device of any of the preceding claims, the electrode assembly includes a first arm and a second arm, wherein the first and second arms include a straightened configuration wherein the first and second arm are adjacent to each other and a splayed configuration wherein the first and second arm are separated from each other, each of the first arm and the second arm including an electrode configured to resect a portion of the leaflet to be resected.

In a sixteenth example, in the valve leaflet resection device of the fifteenth example, the first and second arms are formed of shape memory material and are shape set to the splayed configuration.

In a seventeenth example, the valve leaflet resection device of the fifteenth example or the sixteenth example further includes a balloon nested between the first and second arms of the electrode assembly, wherein the balloon is configured to be inflated to separate the first and second arms into the splayed configuration.

In an eighteenth example, the valve leaflet resection device of any the fifteenth example or the sixteenth example further includes a shaft including an enlarged distal end, wherein the shaft is slidable relative to the electrode assembly, and wherein the shaft is configured to be advanced to drive the enlarged distal end between the first and second arms to splay the first and second arms to the splayed configuration.

In a nineteenth example, the valve leaflet resection device of any one of the fifteenth through eighteenth examples further includes a puncture electrode disposed at a distal end of the electrode assembly with first and second arms in the straightened configuration.

In a twentieth example, a method of resecting a portion of a leaflet includes advancing a leaflet resection device to a first side of a leaflet to be resected, the leaflet to be resected being a native leaflet or a leaflet of an implanted heart valve prosthesis, advancing an electrode assembly of the leaflet resection device through the leaflet such that at least a portion of the electrode assembly is disposed on a second side of the leaflet to be resected, grasping the leaflet to be resected with a leaflet retainer of the leaflet resection device; activating the electrode assembly to remove a portion of the leaflet to be resected while the leaflet retainer is grasping the portion of the leaflet to be resected, and retracting the leaflet retainer with the portion of the resected leaflet into a leaflet capture basket.

BRIEF DESCRIPTION OF DRAWINGS

The details of one or more aspects of the disclosure are set forth in the accompanying drawings and the description below. Other features, objects, and advantages of the techniques described in this disclosure will be apparent from the description and drawings, and from the claims.

The accompanying drawings, which are incorporated herein and form a part of the specification, further serve to explain the principles of the present disclosure and to enable a person skilled in the pertinent art to make and use the embodiments of the present disclosure. The drawings may not be to scale.

DETAILED DESCRIPTION

Figure 1:
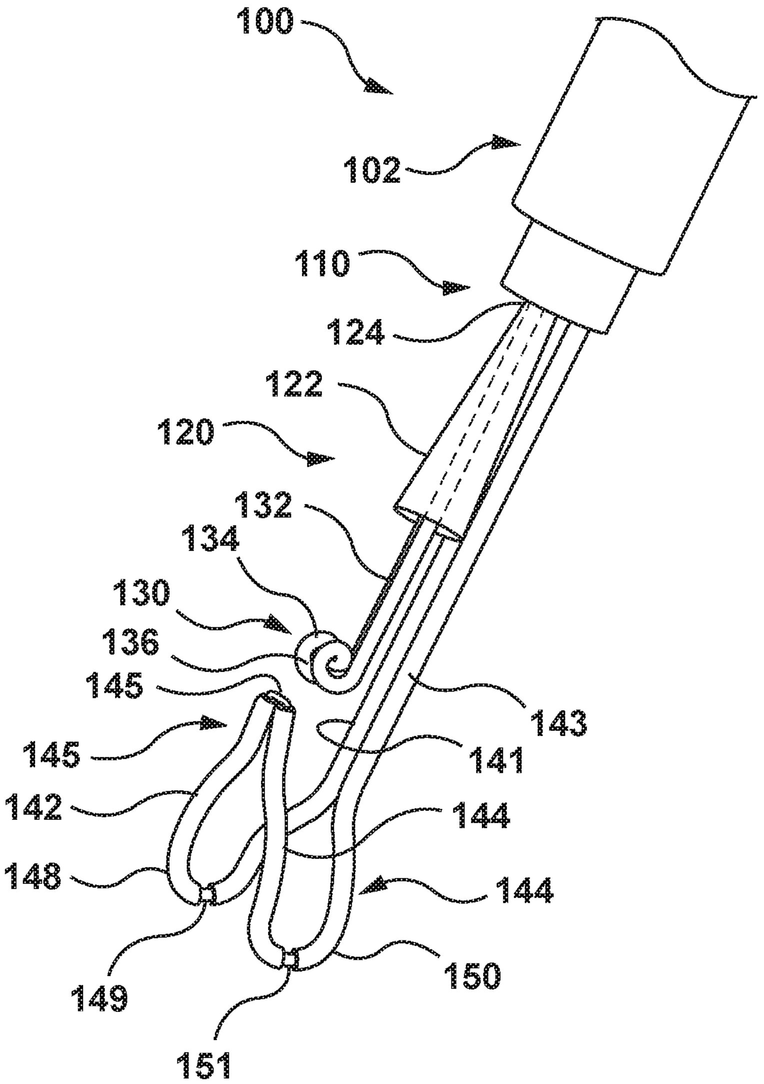
FIG. 1 shows a schematic perspective view of a distal portion of a leaflet resection device according to an embodiment hereof.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a delivery device. The following detailed description is merely exemplary in nature and is not intended to limit the invention of the application and uses of the invention. Furthermore, there is no intention to be bound by any expressed or implied theory presented in the preceding field of the invention, background, summary or the following detailed description.

As used in this specification, the singular forms “a”, “an” and “the” specifically also encompass the plural forms of the terms to which they refer, unless the content clearly dictates otherwise. The term “about” is used herein to mean approximately, in the region of, roughly, or around. When the term “about” is used in conjunction with a numerical range, it modifies that range by extending the boundaries above and below the numerical values set forth. In general, the term “about” is used herein to modify a numerical value above and below the stated value by a variance of 20%. It should be understood that use of the term "about" also includes the specifically recited number of value.

The terms "proximal" and "distal" herein are used with reference to the clinician using the devices. Therefore, "proximal" and "proximally" mean in the direction toward the clinician, and "distal" and "distally" mean in the direction away from the clinician.

Embodiments hereof relate to a leaflet resection device or tool configured to resect one or more leaflets of a heart valve. Embodiments described herein are particularly related to a leaflet resection device resecting a section of a leaflet of a previously implanted transcatheter heart valve prosthesis. However, the leaflet resection devices described herein may also be used to resect a section of a leaflet of a previously implanted surgical heart valve prosthesis and/or a section of a leaflet of a native heart valve.

Referring now to FIGS. 1-8E, a leaflet resection device 100 is shown. The leaflet resection device 100 includes an outer, delivery catheter 102, an inner catheter 110, a resected leaflet capture basket 120, a leaflet retainer 130, and an electrode assembly 140. The outer, delivery catheter 102 includes a lumen 104 and may be a steerable catheter, as will be explained in more detail below.

Figure 2:
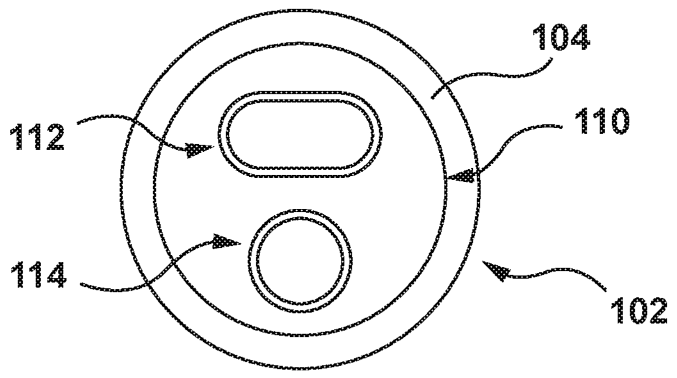
FIG. 2 shows a cross-section of the outer and inner catheters of the leaflet resection device of FIG. 1.

The inner catheter 110 is slidably disposed within the lumen 104 of the outer, delivery catheter 102. As shown in FIG. 2, the inner catheter 110 includes a first lumen 112 and a second lumen 114. The first lumen 112 is configured to receive the electrode assembly 140 therein. The second lumen 114 is configured to receive the capture basket 120 and the leaflet retainer 130 therein. The second lumen 114 is also configured to receive the capture basket 120 and the leaflet retainer 130 therein with a resected portion of the leaflet, as described in more detail below.

Figure 6A:
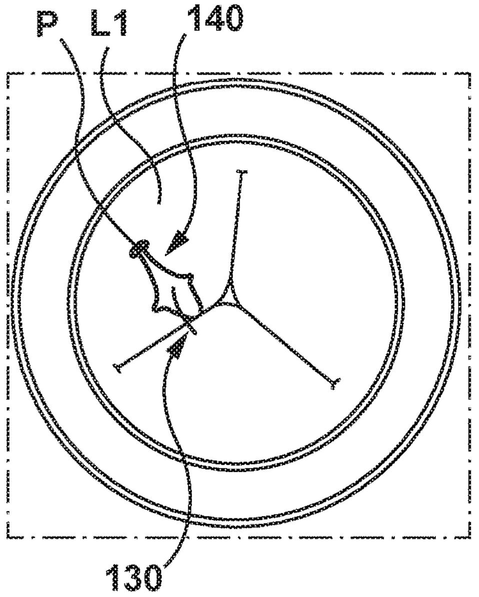
FIGS. 6A-6C show views of a leaflet retainer of the leaflet resection device of FIG. 1 puncturing and grasping a leaflet of a transcatheter heart valve prosthesis.
Figure 6B:
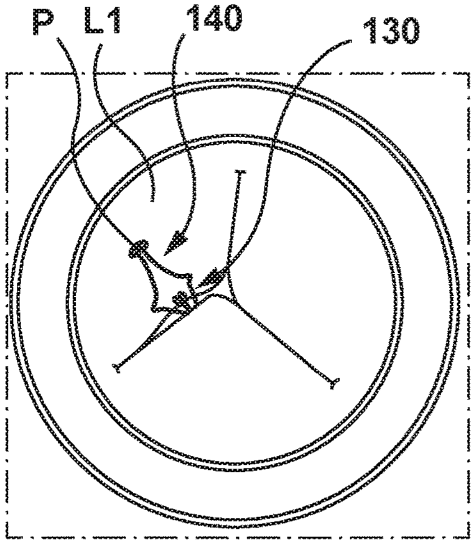
Figure 6C:
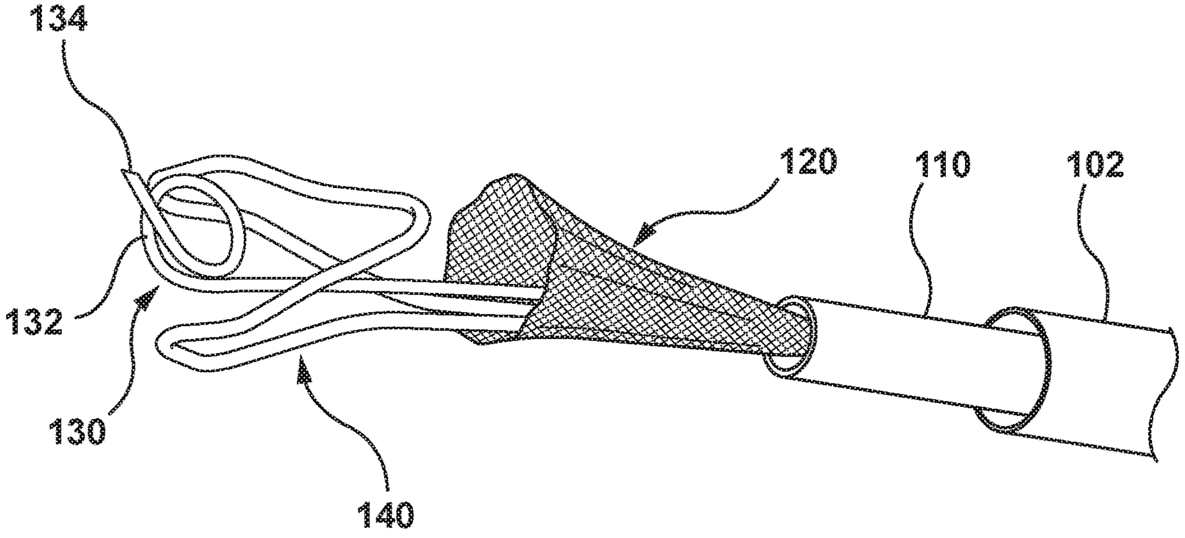

The leaflet retainer 130 is slidably disposed within the second lumen 114 of the inner catheter 110. The leaflet retainer 130 may be a wire 132 including a hook 134 at a distal end thereof. In some embodiments, such as shown in FIGS. 6A-6C, the wire 132 may be shape set to form the hook 134 at the distal end thereof as the wire 132 is distally advanced out of the lumen 114. Thus, the wire 132 is substantially parallel to a central longitudinal axis of the lumen 114 when the wire 132 is disposed therein. However, when the wire 132 exits the lumen 114, the distal end of the wire 132 forms the hook 134 to grasp the leaflet to be resected. The wire may also include an electrode 136 at the distal end thereof. The electrode 136 may be an RF electrode and may be used to pierce the leaflet to be resected, as explained in more detail below.

The resected leaflet capture basket 120 is configured to receive the resected portion of the leaflet therein. The capture basket 120 is slidably disposed in the second lumen 114 of the inner catheter 110 for delivery to the treatment site. The capture basket 120 includes a radially compressed configuration when disposed within the second lumen 114. When the capture basket 120 is distally advanced out of the second lumen 114, the capture basket 120 expands to a radially expanded configuration configured to receive the resected leaflet therein. In the embodiment of FIGS. 1-6C, the capture basket 120 is disposed co-axially around the wire 132 of the leaflet retainer 130. In the embodiment shown in FIGS. 1-6C, the capture basket 120 is a tapered mesh tube having a distal end with a first dimension transverse to the central longitudinal axis larger than a second dimension transverse to the central longitudinal axis at the proximal end thereof smaller than the first dimension. The proximal end of the tapered mesh tube may be in contact with the wire 132 of the leaflet retainer 130. The capture basket 120 may further include a wire or tube (not shown) extending to a proximal end of the delivery system to translate the capture basket 120 distally out of the second lumen 114 and proximally back into the second lumen 114. Other actuation devices may be also be used to advance and retract the capture basket 120.

The electrode assembly 140 includes a first arm 142 and a second arm 144. In the embodiment shown, the first and second arms 142, 144 are made of a shape memory material (e.g., a shape memory metal such as nitinol) and are shape set to the open or splayed configuration shown in FIG. 1. The first and second arms 142, 144 are joined at their terminal ends 145. In the embodiment shown in FIGS. 1-6C, the joined terminal ends 145 may include an electrode 146, which may also be referred to as a leaflet traversing electrode. The electrode 146 may be used to assist the electrode assembly 140 to pass from a downstream side to an upstream side of the leaflet to be resected, as explained below.

Each of the first and second arms 142, 144 may be the distal portion of a respective first and second wire 141, 143. Thus, in the open or splayed configuration, a proximal portion of the first wire 141 extends longitudinally. The distal portion of the first wire 141 is the first arm 142, and it extends radially outwardly and bends at a first bend 148 in generally back toward the proximal portion. Therefore, the first bend 148 may be approximately 180 degrees. Similarly, in the open or splayed configuration, a proximal portion of the second wire 143 extends longitudinally. The distal portion of the second wire 143 is the second arm 144, and it extends radially outwardly opposite the first wire 141 and bends at a second bend 150 generally back toward the proximal portion. Therefore, the second bend 148 may be approximately 180 degrees. First and second electrodes 149, 151 are disposed at the first and second bends 148, 150, respectively. The first and second electrodes 149, 151 operate to resect a chunk of the leaflet of interest, as explained below.

Figure 3:
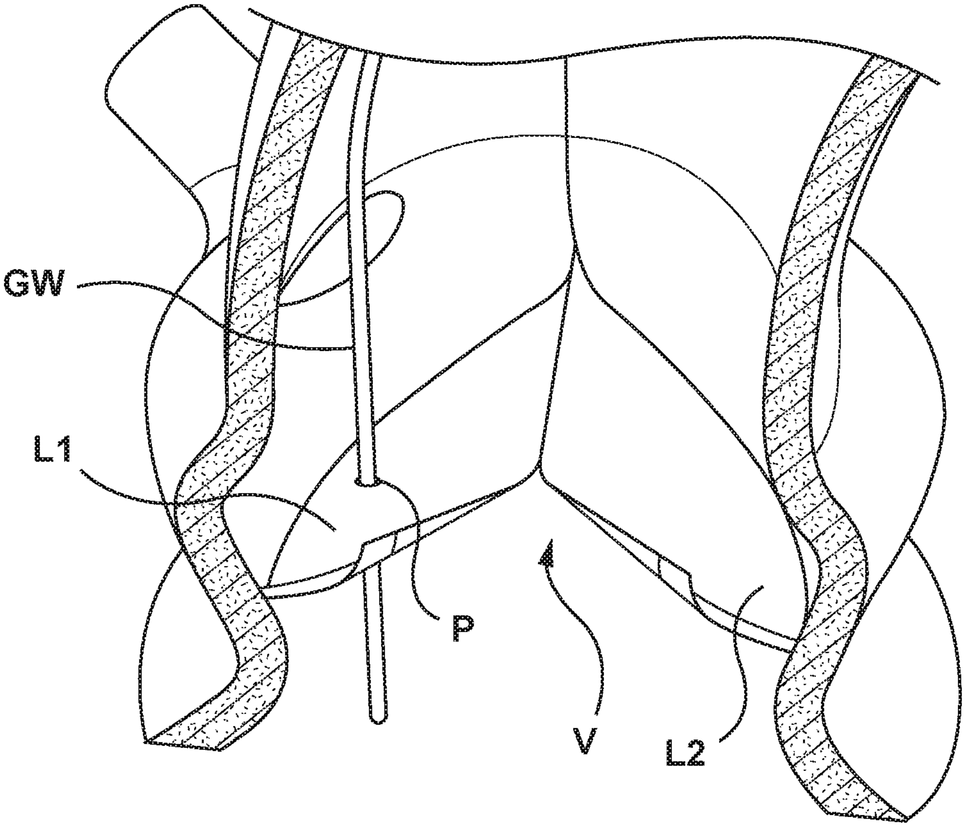
FIG. 3 shows a native aortic valve with a guide-wire puncturing a leaflet thereof.
Figure 4:
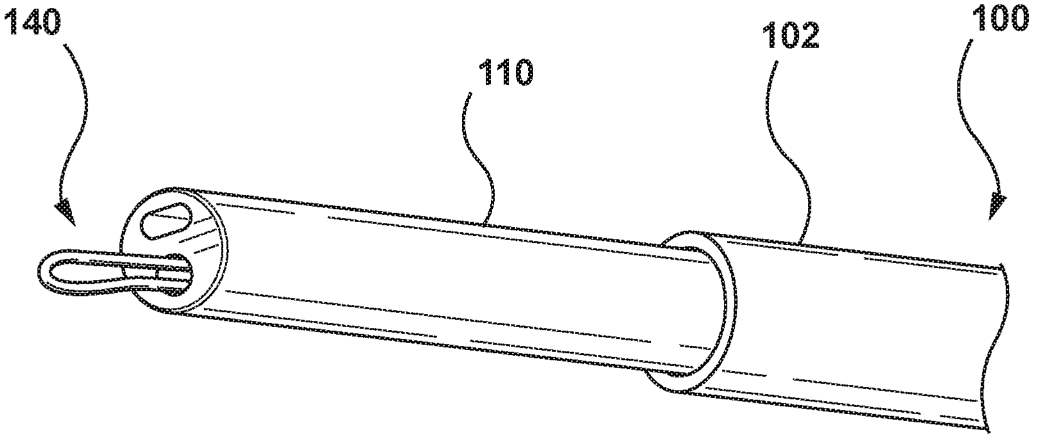
FIG. 4 shows the leaflet resection device of FIG. 1 with an electrode assembly thereof partially extending from an inner catheter thereof.

An embodiment of use of the leaflet resection device 100 to resect a leaflet will now be explained with respect to FIGS. 3-8C. A guide catheter (not shown) can be delivered via a retrograde approach to the leaflet L1 of interest to be resected/removed. In FIG. 3, the leaflet L1 to be resected is a native leaflet of a native aortic valve. However, as explained above, this is not meant to be limiting, and FIGS. 5A-8C show the leaflet resection device in operation to resect a leaflet L1 of a transcatheter heart valve prosthesis THV. A guidewire GW may be advanced through the guide catheter to the leaflet L1 and directed to puncture (i.e. create a hole in) the leaflet L1 with the approach as is generally depicted in FIG. 2. The guide wire GW can be a standard guide wire or can be an electrified guide wire having an exposed electrode tip that can be introduced via the guide catheter, for example. The guide catheter can be a separate catheter or the delivery catheter 102 can be disposed with a guide wire lumen and provide the same function as the described guide catheter.

Once the puncture P is made, several options for placement of the leaflet resection device 100 are possible. In one embodiment, the guide wire GW and the guide catheter are both removed and the delivery catheter 102 is advanced and brought to (or even through), the puncture P in the respective leaflet. L1 In another embodiment, the guide wire GW is maintained in position through the leaflet L1 and the guide catheter is removed. Then, the delivery catheter 102 is delivered over the guide wire GW to ensure the delivery catheter 102 is in position at (or even through) the leaflet puncture P. In yet another embodiment, the guide catheter is advanced to (or through the puncture P) and the guide wire GW is removed. Then, the delivery catheter 102 is delivered through the guide catheter, which is then removed and the delivery catheter 102 is then in position. In yet another embodiment, the delivery catheter 102 provides the guide catheter function and thus eliminates the need to exchange the guide catheter with the delivery catheter 102.

Alternatively, the electrode 136 at the distal end of the leaflet retainer 130 may be used to create the hole or puncture P in the leaflet L1. In another alternative, the electrode assembly 140 may be used to create the puncture P in the leaflet L1. In one embodiment, the electrode 146 at the distal end of the electrode assembly 140 may be used to create the hole or puncture in the leaflet L1. In such an embodiment, the electrode assembly 140 is disposed within the first lumen 112 of the inner catheter 110 such that the first and second arms 142, 144 are straightened. Thus, the electrode 146 is facing the opening at the distal end of the inner catheter 110 when the electrode assembly exits the inner catheter 110, the electrode 146 can be energized to create the puncture. In another embodiment, the first and second electrodes 149, 151 may be used to create the puncture P. In such an embodiment, first and second arms 142, 144 are constrained within the inner catheter 110 such that when they exit the inner catheter 110, they behave like a single electrode and can be energized to create the puncture P.

In some embodiments, after the puncture P is formed, the delivery catheter 102 is delivered over the guide wire GW in a delivery arrangement to a location adjacent the leaflet L1. In other embodiments, the puncture P need not be formed. The inner catheter 110 in a delivery arrangement (i.e., with the electrode assembly 140, the leaflet retainer 130, and the leaflet capture basket 110 disposed within the inner catheter 110) may that be advanced through the delivery catheter 102 to the location of the puncture P so that the distal end of the inner catheter 110 is adjacent the leaflet L1.

Figure 5A:
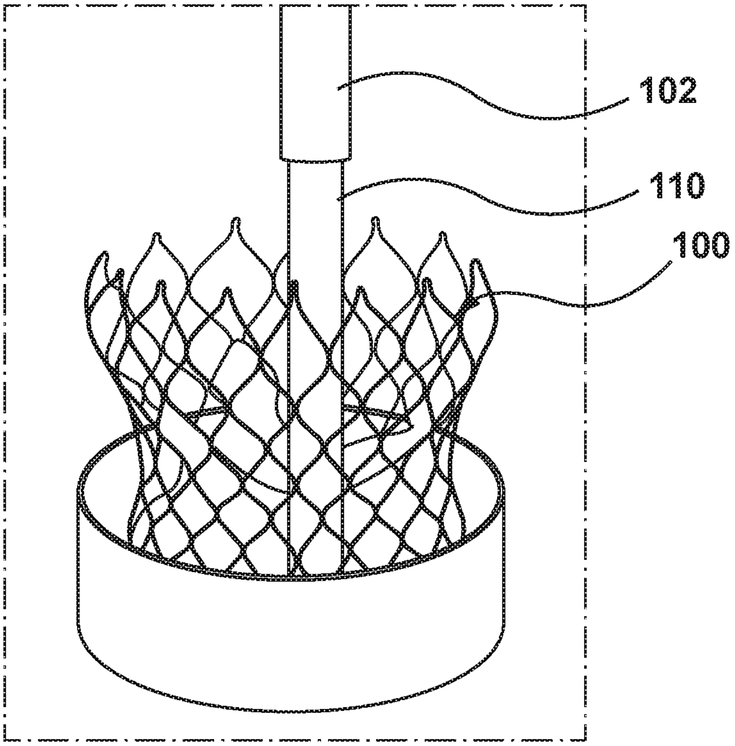
FIGS. 5A-5B shows views of the electrode assembly of the leaflet resection device of FIG. 1 puncturing a leaflet of a transcatheter heart valve prosthesis.
Figure 5B:
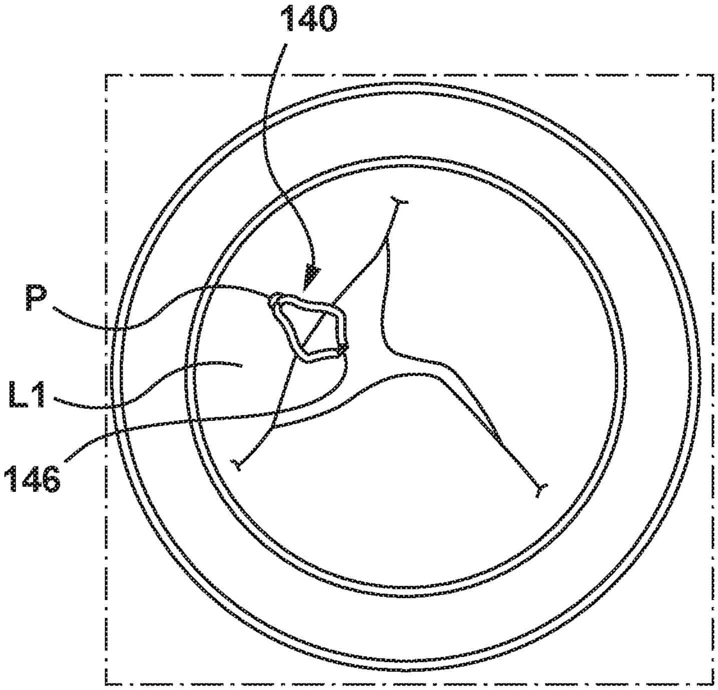

Once the inner catheter 110 is in position, the electrode assembly 140 is advanced from the downstream side of the leaflet L1 to the upstream side of the leaflet L1, as shown in FIGS. 5A-5C. The electrode assembly 140 may be advanced through a previously created puncture (such as by the guide wire GW) or may create its own puncture P through which it is advanced, as shown in FIGS. 5A and 5B.

The leaflet retainer 130 is then advanced through the leaflet L1. It can be advanced through the puncture P or the leaflet retainer 130 my create its own puncture through which it advances, for example, using the electrode 136. In other embodiments, the leaflet retainer 130 may have a sharp tip to puncture the leaflet 130. FIG. 6A shows the leaflet retainer 130 advanced through the leaflet L1 but still relatively straight. As the leaflet retainer 130 continues to be advance from the inner catheter 110, the distal end thereof curls to grasp the leaflet L1, as shown in FIG. 6B. FIG. 6C shows the leaflet resection device 100 at this juncture and with the capture basket 130 in the open configuration.

Figure 7A:
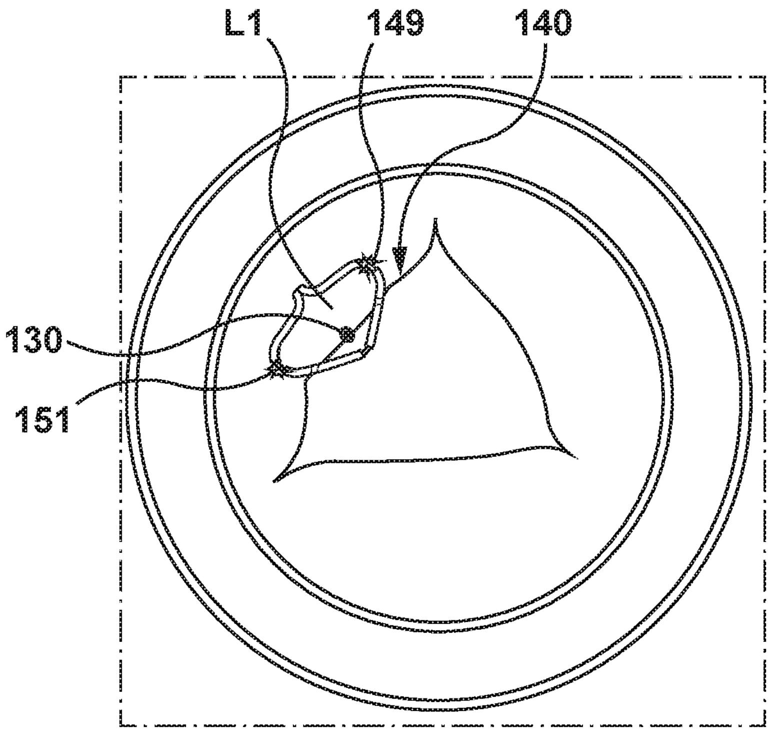
FIGS. 7A-7B show views of the electrode assembly of the leaflet resection device of FIG. 1 resecting a portion of a leaflet of a transcatheter heart valve prosthesis.
Figure 7B:
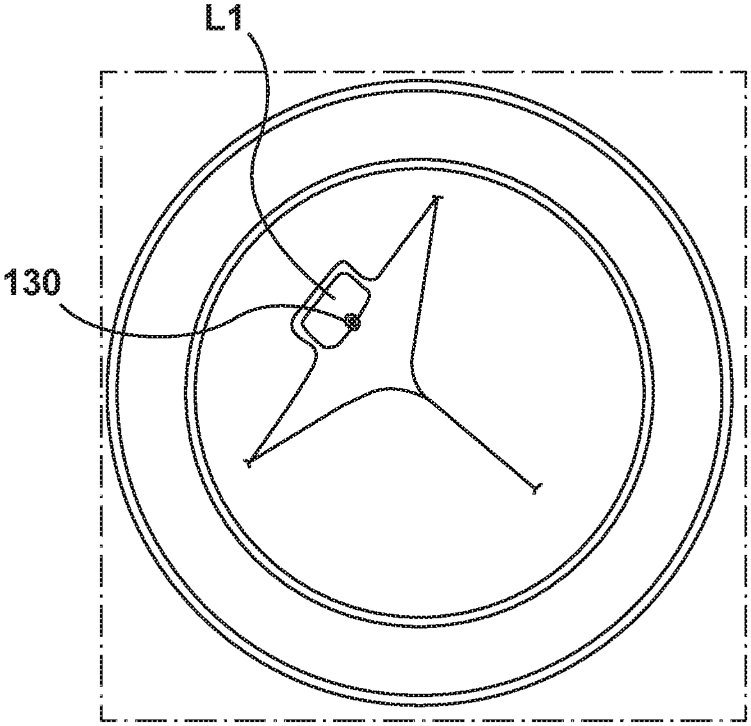

As explained above, the arms 142, 144 of the electrode assembly 140 may be shape set so as to splay upon traversal of the leaflet L1. However, in some instances, the electrodes 149, 151 may need to briefly energized to assist in splaying the arms, as shown in FIG. 7A. With the arms 142, 144 splayed, and the leaflet retainer 130 grasping the leaflet L1, the electrodes 149, 151 are energized and the electrode assembly is pulled to remove a section of the leaflet L1, as shown in FIG. 7B. Thus, FIG. 7B shows the removed portion of the leaflet L1 with the leaflet retainer 130 grasping the leaflet L1. The electrode assembly 140 has been pulled proximally and is not shown in FIG. 7B for clarity.

Figure 8A:
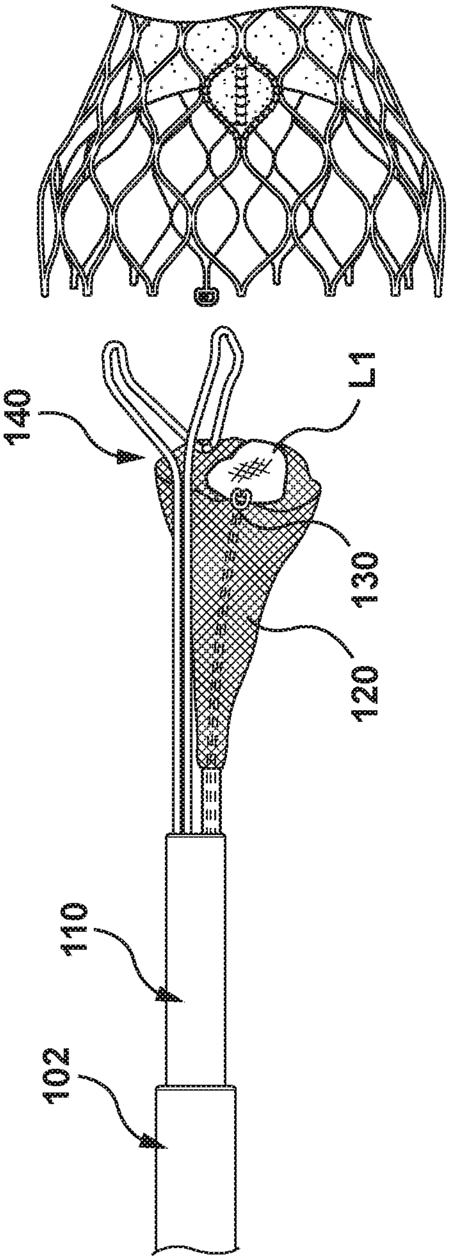
FIGS. 8A-8E show views of the resected portion of the leaflet the transcatheter heart valve prosthesis being retracted into the leaflet retraction device of FIG. 1.
Figure 8B:
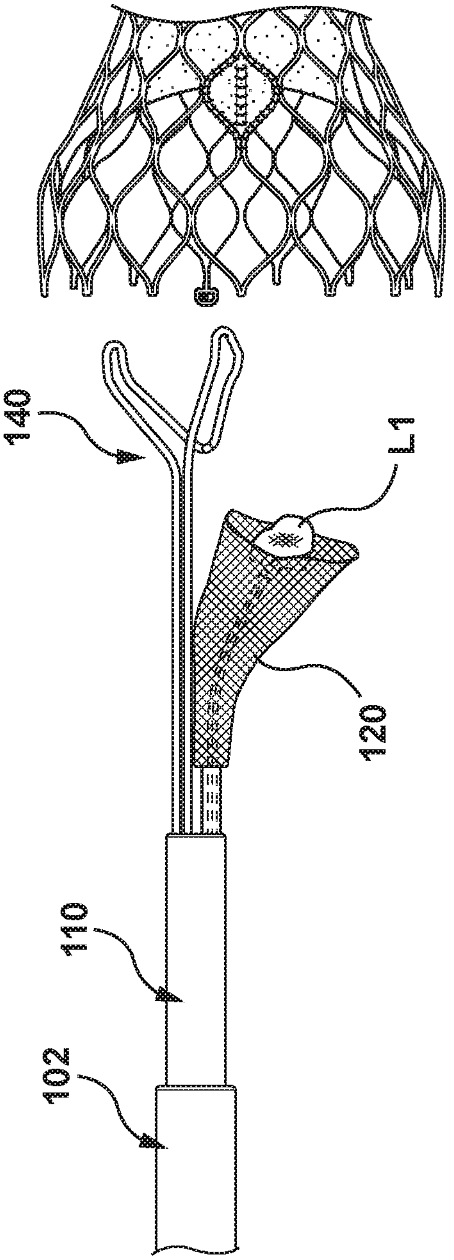
Figure 8C:
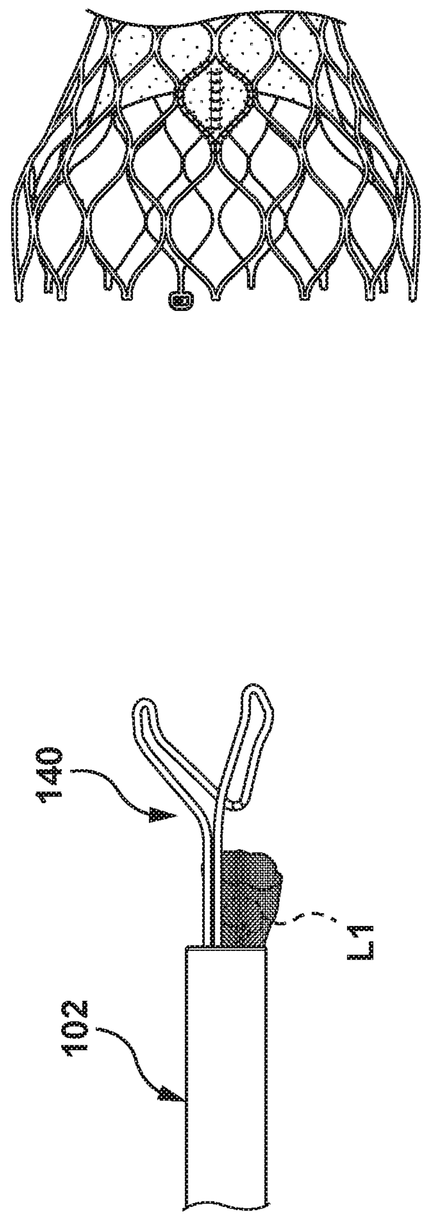
Figure 8E:
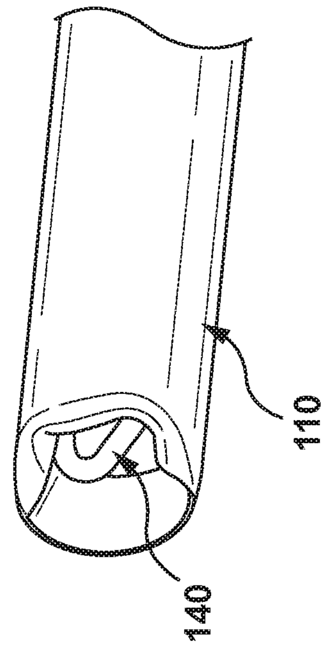
Figure 8D:
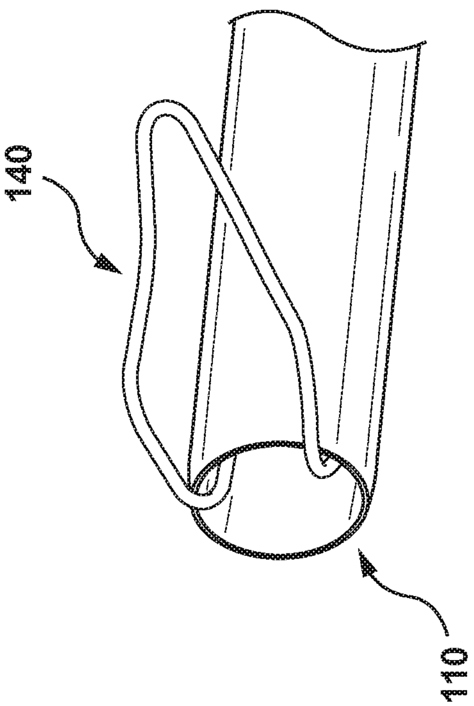

With the resected portion of the leaflet L1 held by the leaflet retainer 130, the electrode assembly 140 and the leaflet retainer are retracted proximally to the upstream side of the valve, as shown in FIG. 8A. The leaflet retainer 130 continues to be retracted proximally relative to the capture basket 120 until the resected portion of the leaflet is disposed within the capture basket 120, as shown in FIG. 8B. The leaflet retainer 130 and the capture basket 120 are then retracted proximally into the second lumen 114 of the inner catheter as the electrode assembly 140 is retracted into the first lumen 112 of the inner catheter 110, as shown in FIGS. 8C-8E.

The leaflet resection device 100 can then be removed from the patient with the resected portion of the leaflet L1 disposed within the second lumen 114 of the inner catheter.

Although a particular embodiment of the leaflet resection device 100 has been shown and described, this is not meant to be limiting, and the features described may be modified in keeping with the principles described herein.

Figure 9:
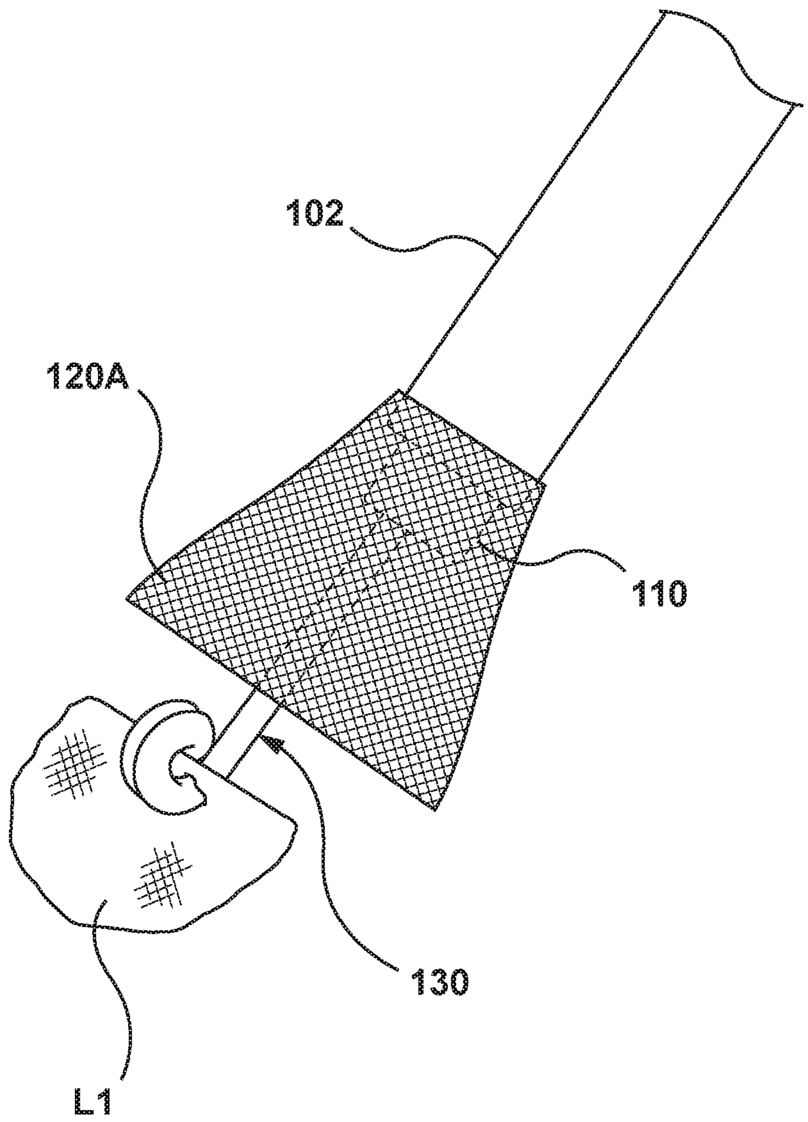
FIG. 9 shows a retracted leaflet capture basket in accordance with an embodiment hereof.

For example, and not by way of limitation, instead of the resected leaflet capture basket 120 being coaxially disposed around the leaflet retainer 130, a resected leaflet capture basket 120A may be attached to the delivery catheter 102, as shown in FIG. 9. In such an embodiment, upon resection of the leaflet, the leaflet retainer 130 with the resected leaflet is retracted into the capture basket 120A and the delivery catheter 102.

Figure 10A:
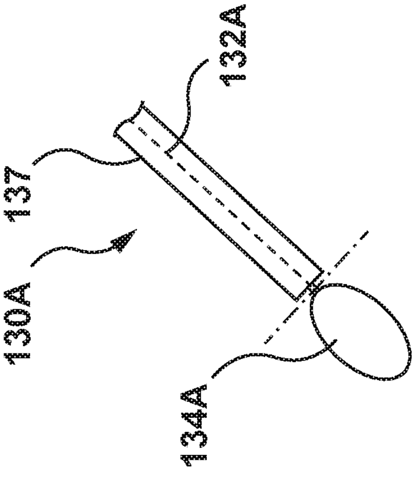
FIGS. 10A-10C show leaflet retainers according to embodiments hereof.
Figure 10B:
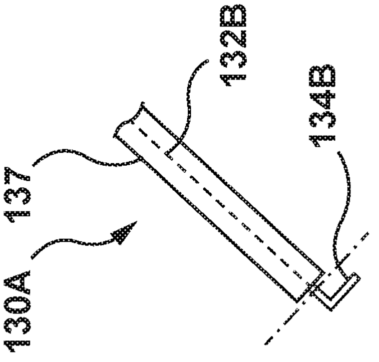
Figure 10C:
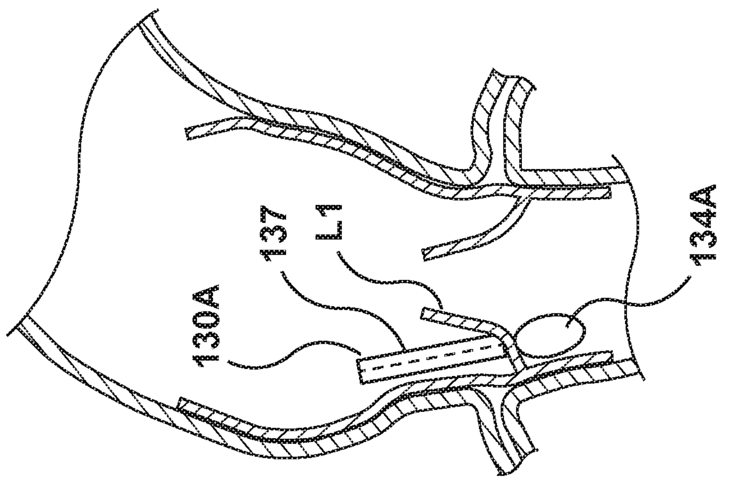

In another example, instead of the leaflet retainer 130 shown in FIG. 1, a leaflet retainer 130A may include a tube 137 with a balloon 134A slidably disposed within the tube 137, as shown in FIG. 10A. In use, the tube 137 may be advanced to the downstream side of the leaflet L1. The balloon 134A in an uninflated state may traverse the leaflet L1, such as through a puncture P. The balloon 134A may then be inflated to an inflated state such that the leaflet L1 is captured between the inflated balloon 134A and the tube 137, as shown in FIG. 10C. Upon resection of a portion of the leaflet L1, the portion is held by the leaflet retainer 130A and then retracted into the resected leaflet capture basket, as explained above. FIG. 10B shows a similar embodiment of a leaflet retainer 130B except that instead of the balloon 134A, and wire 132B with a shape set tip 134B is disposed within the tube 137. In use, the tube 137 may be advanced to the downstream side of the leaflet L1. The wire 102B is advanced so that the tip 134B advances through the leaflet L1. Upon traversal of the leaflet L1, the shape set tip 134B bends so at to capture the leaflet L1 between the tip 134B and the tube 137, as shown in FIG. 10B.

Figure 11A:
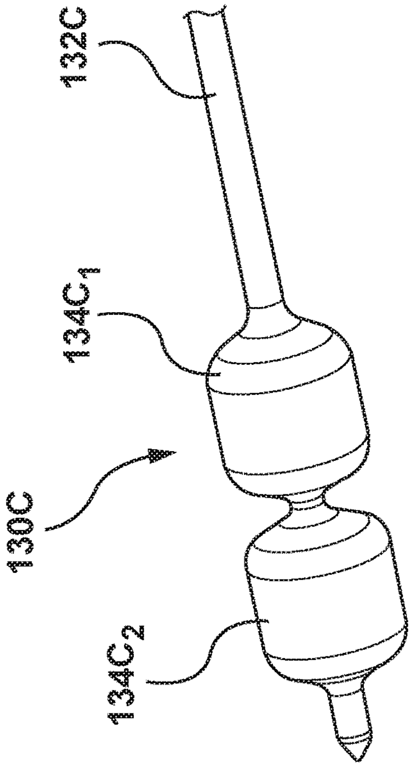
FIGS. 11A-11C show leaflet retainers according to embodiments hereof.
Figure 11B:
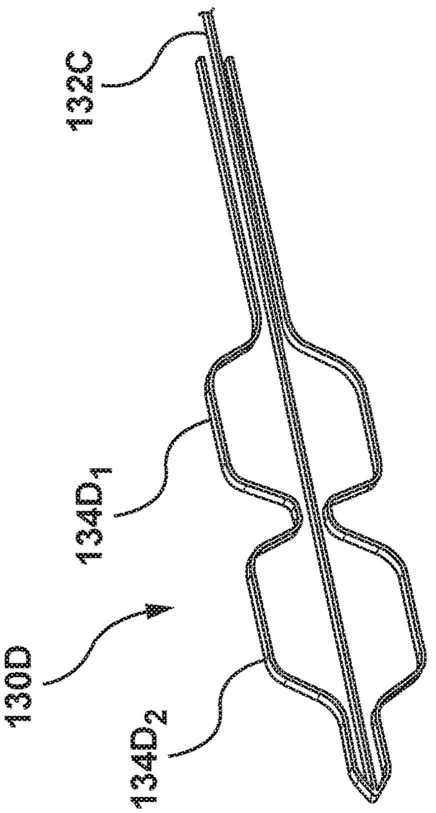
Figure 11C:
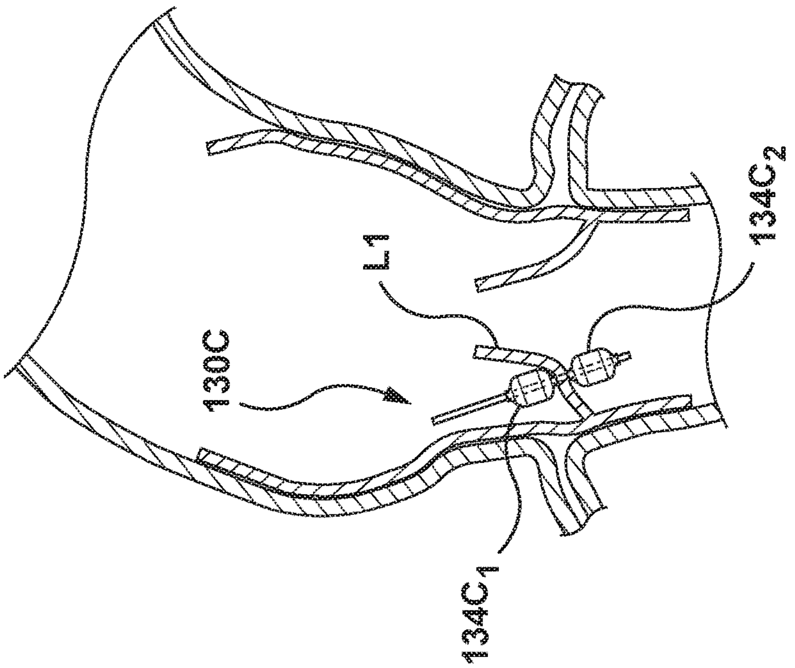

In another example, instead of the leaflet retainer 130 of FIG. 1, a leaflet retainer 130C may include a proximal balloon 134$C_1$ and a distal balloon 134$C_2$ disposed on a shaft 132C. The shaft 132C is advanced with the balloons 134$C_1$ and 134$C_2$ uninflated such that the distal balloon traverses from the downstream side to the upstream side of the leaflet L1, such as through a puncture. The balloons 134$C_{12}$, 134$C_2$ are then inflated such that the leaflet L1 is captured between distal balloon 134$C_2$ and the proximal balloon 134$C_2$, as shown in FIG. 11C. The embodiment of FIG. 11A can also be referred to as a “dog-bone” balloon. Upon resection of a portion of the leaflet L1, the portion is held by the leaflet retainer 130C and then retracted into the resected leaflet capture basket, as explained above. Similarly, FIG. 11B shows a leaflet retainer 130D utilizing similar principles of the leaflet retainer 130C, but with utilizing a wire structure. Therefore, the leaflet retainer 130D includes a wire 132C, and a retainer portion that includes a proximal radial bump $134D_1$ and a distal radial bump $134B_2$. The wire 132C is advanced within the second lumen 114 of the inner catheter 110, for example, such that proximal and distal bumps $134D_1$ and $134D_2$ are substantially parallel to the wire 132D, or radially collapsed. The wire 132D is advanced such that the distal bump $132D_2$ traverses from the downstream side to the upstream side of the leaflet L1, such as through a puncture. The shape set of the proximal and distal bumps $134D_1$, $134D_2$ enables them to radially expand as they exit the second lumen 114. Thus, the leaflet L1 is captured between distal bump $134D_2$ and the proximal bump $134D_1$, similar to the dog-bone balloon embodiment. Upon resection of a portion of the leaflet L1, the portion is held by the leaflet retainer 130D and then retracted into the resected leaflet capture basket, as explained above.

Figure 12B:
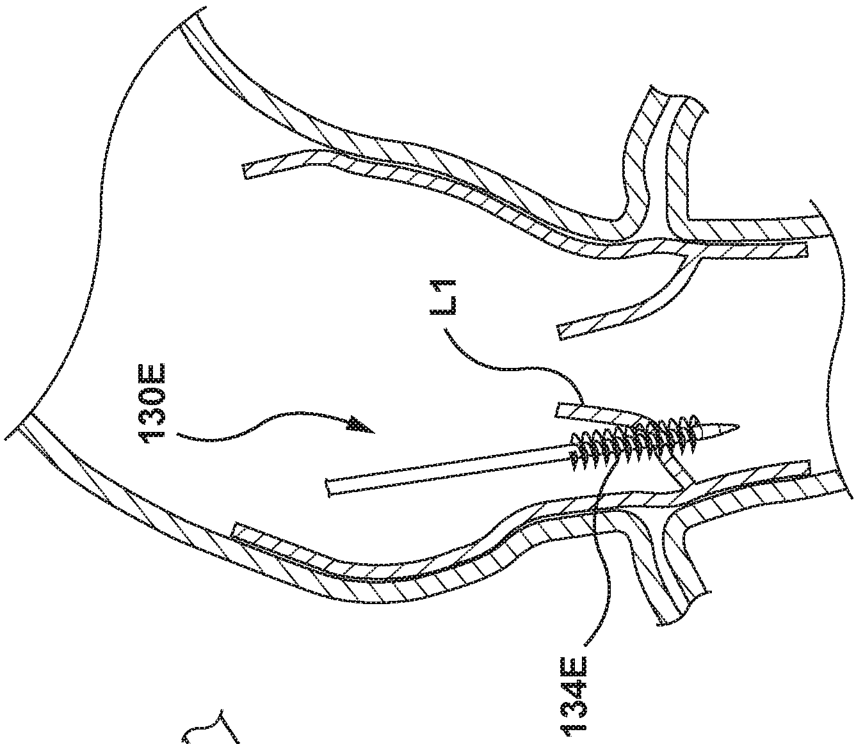
FIGS. 12A-12B show a leaflet retainer according to an embodiment hereof.
Figure 12A:
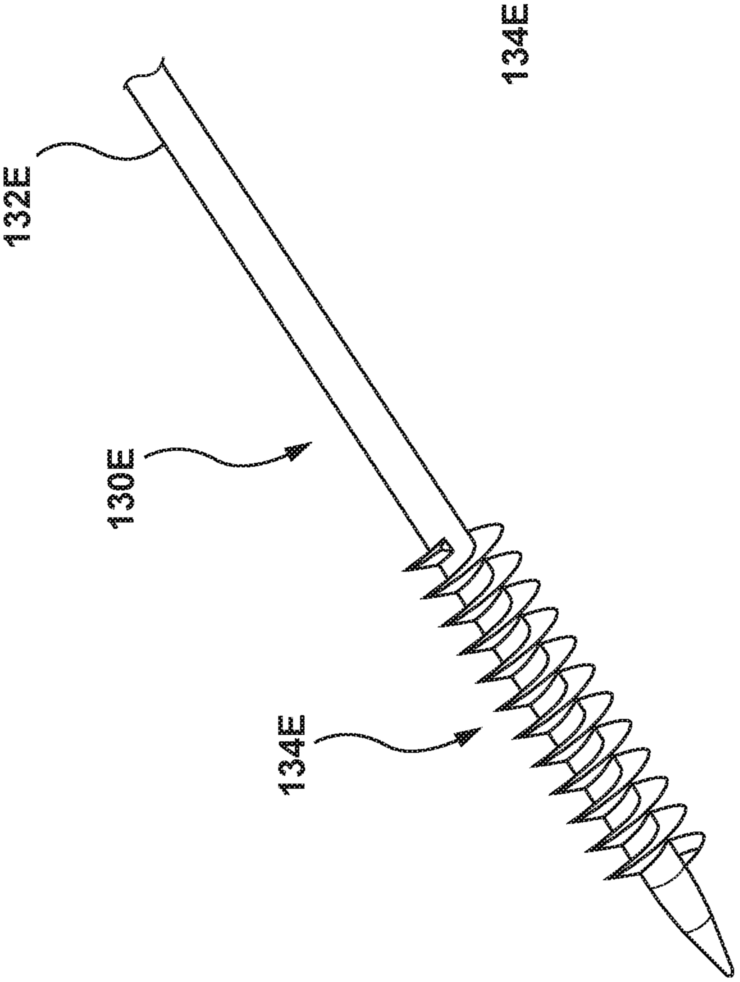

In another example, instead of the leaflet retainer 130 of FIG. 1, a leaflet retainer 130E may include a shaft or wire 132E and an auger or helical coil 134E at a distal end thereof, as shown in FIGS. 12A and 12B. The shaft 132E is advanced through the leaflet L1 such that a portion of the auger is downstream of the leaflet L1 and a portion of the auger 134E is upstream of the leaflet L1, thereby grasping the leaflet L1, as shown in FIG. 12B. Upon resection of a portion of the leaflet L1, the portion is held by the leaflet retainer 130E and then retracted into the resected leaflet capture basket, as explained above.

Figure 13A:
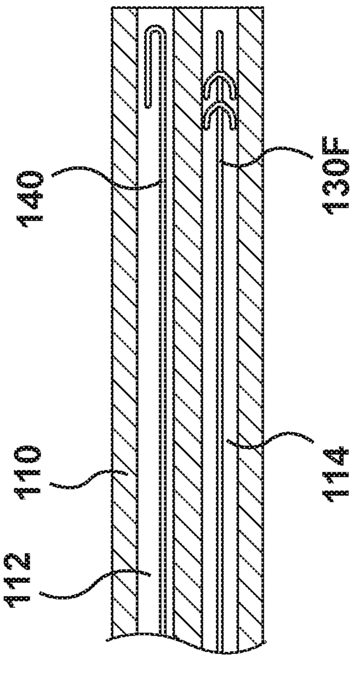
FIGS. 13A-13C shows a leaflet retainer according to an embodiment hereof.
Figure 13B:
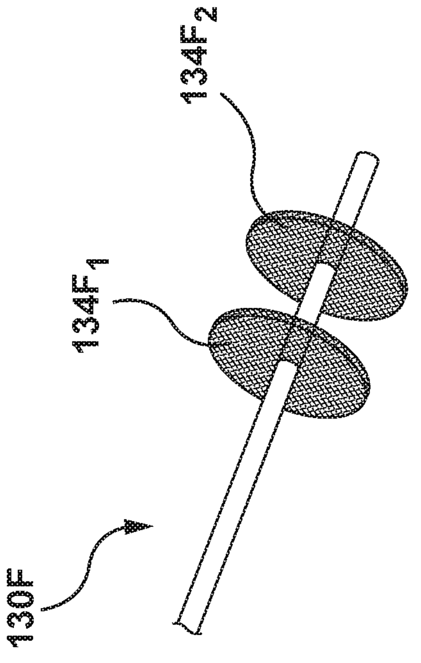
Figure 13C:
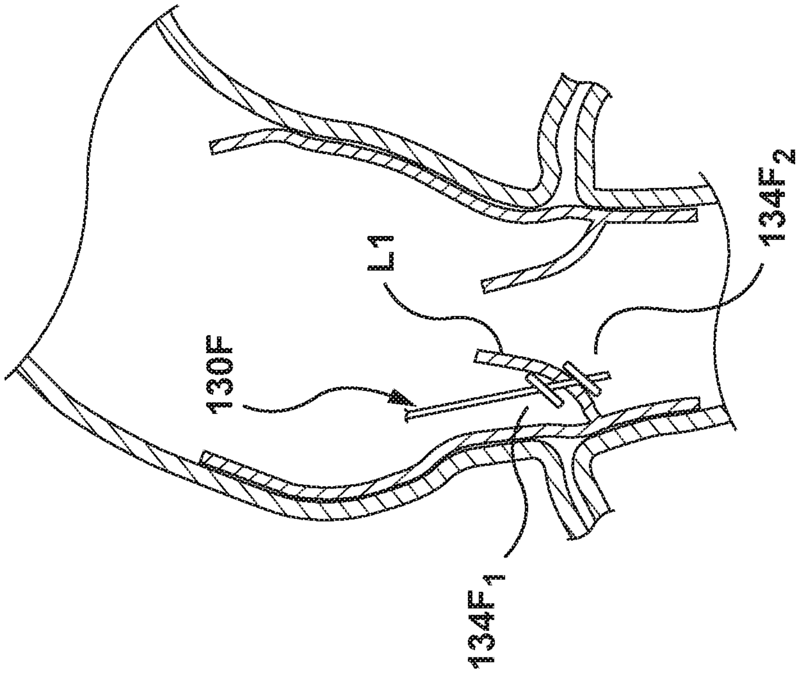

In another example, shown in FIGS. 13A-13C, instead of the leaflet retainer 130 of FIG. 1, a leaflet retainer 130F may include a proximal retainer $134F_1$ and a distal retainer $134F_2$ disposed on a shaft 132F. The shaft 132F is advanced in the second lumen 114 of the inner catheter 110 with the retainers $134F_1$ and $134F_2$ radially compressed, as shown in FIG. 13A. The inner catheter 110 is advanced to the downstream side of the leaflet L1. The leaflet retainer 130F is then advanced through the leaflet L1 until the distal retainer $132F_2$ is on the upstream side of the leaflet L1. As the distal and proximal retainers $132F_2$ and $132F_1$ exit the second lumen 114, they radially expand to the radially expanded state, thereby capturing the leaflet F1 therebetween, as shown in FIGS. 13B and 13C. Upon resection of a portion of the leaflet L1, the portion is held by the leaflet retainer 130F and then retracted into the resected leaflet capture basket, as explained above.

Figure 15:
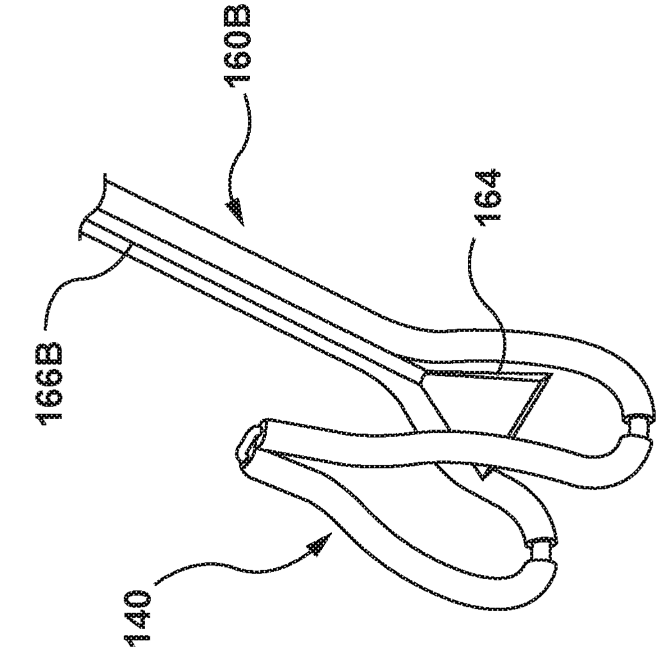
FIG. 15 shows a splaying device to assist in opening an electrode assembly of a leaflet resection device according to an embodiment hereof.
Figure 14:
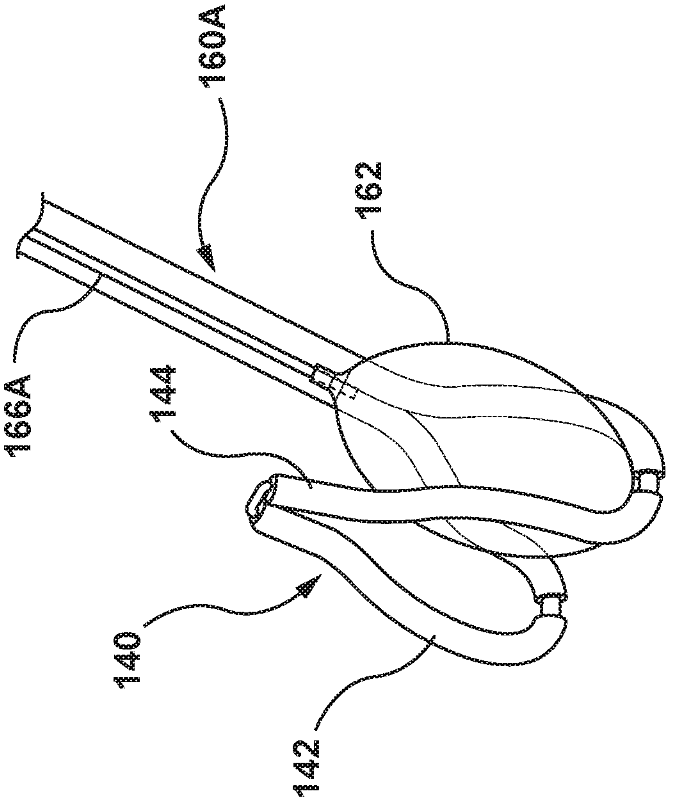
FIG. 14 shows a splaying device to assist in opening an electrode assembly of a leaflet resection device according to an embodiment hereof.

In another example, the electrode assembly 140 as described above is shape set to splay outwardly, and the electrodes thereon may be used to assist in opening the arms of the electrode assembly. However, in some instances, such as heavily calcified valves, a splay assist device may be used to assist in opening the electrode assembly 140. FIG. 14 shows an example of a splay assist device 160A, including a shaft 166A with a balloon 162 at a distal end thereof nested between the arms 142, 144 of the electrode assembly. During the procedure as described above, the balloon 162 may be inflated to splay the arms 142, 144 open to ensure that a sufficiently large piece of the leaflet is resected by the electrode assembly 140. Similarly, FIG. 15 shows another example of a splay assist device 160B, including a shaft 166B with a wedge 164 at a distal end thereof. During the procedure as described above, the shaft 166B may be advanced to drive the wedge 164 between the arms 142, 144 to splay the arms 142, 144 open to ensure that a sufficiently large piece of the leaflet is resected by the electrode assembly 140.

FIGS. 16-20 show various views of features of the leaflet resection device 100 and a delivery system 200 for the leaflet resection device.

Figure 16:
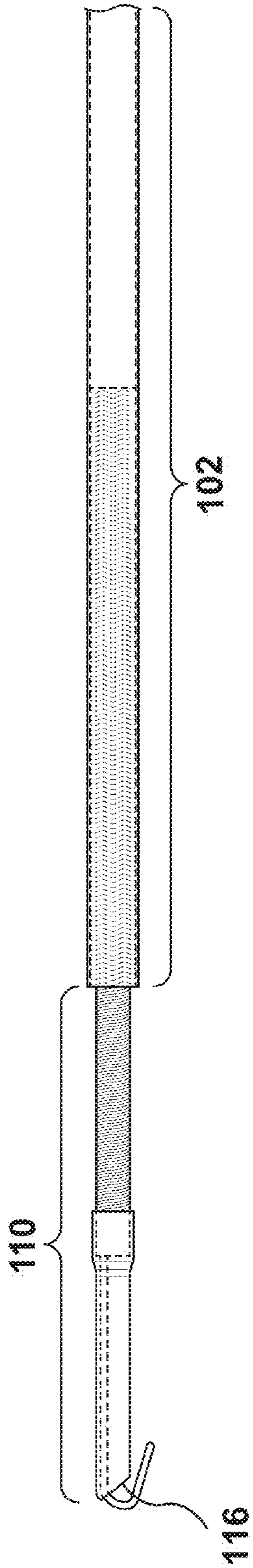
FIGS. 16-20 show views of a delivery system of a leaflet resection device according to embodiments hereof.
Figure 20:
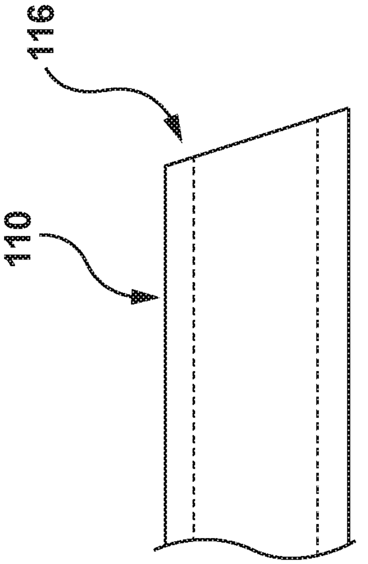

FIG. 16 shows the inner catheter 110 and the outer delivery catheter 102. In an embodiment, the inner catheter 110 is a torqueing catheter in that it is capable of being rotated about its central longitudinal axis. In an embodiment, the delivery catheter 102 is a steering catheter with two pull wires (not shown) enabling the delivery catheter 102 to be steered. Still further, in an embodiment, as shown in FIGS. 16 and 20, a distal end of the inner catheter 110 may include a beveled edge 116. Thus, when delivering the leaflet resection device to the valve leaflet to be resected, the bi-direction delivery catheter 102 steers to the desired aortic cusp by first steering past the great vessel and then having the torqueable inner catheter 110 tracked through the delivery catheter 102. With the inner catheter 110 sticking out of the distal end of the delivery catheter 102, the outer catheter 102 steers to the final leaflet destination with the inner catheter 110 torqued with the beveled edge 116 facing the leaflet L1.

Figure 17:
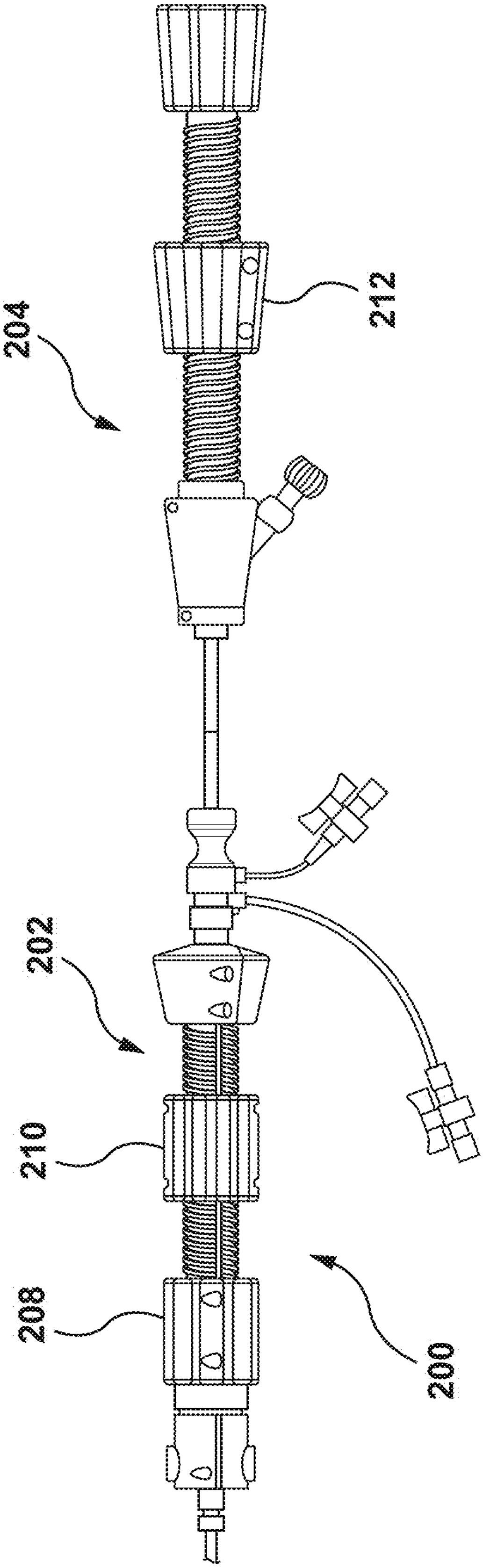
Figure 18:
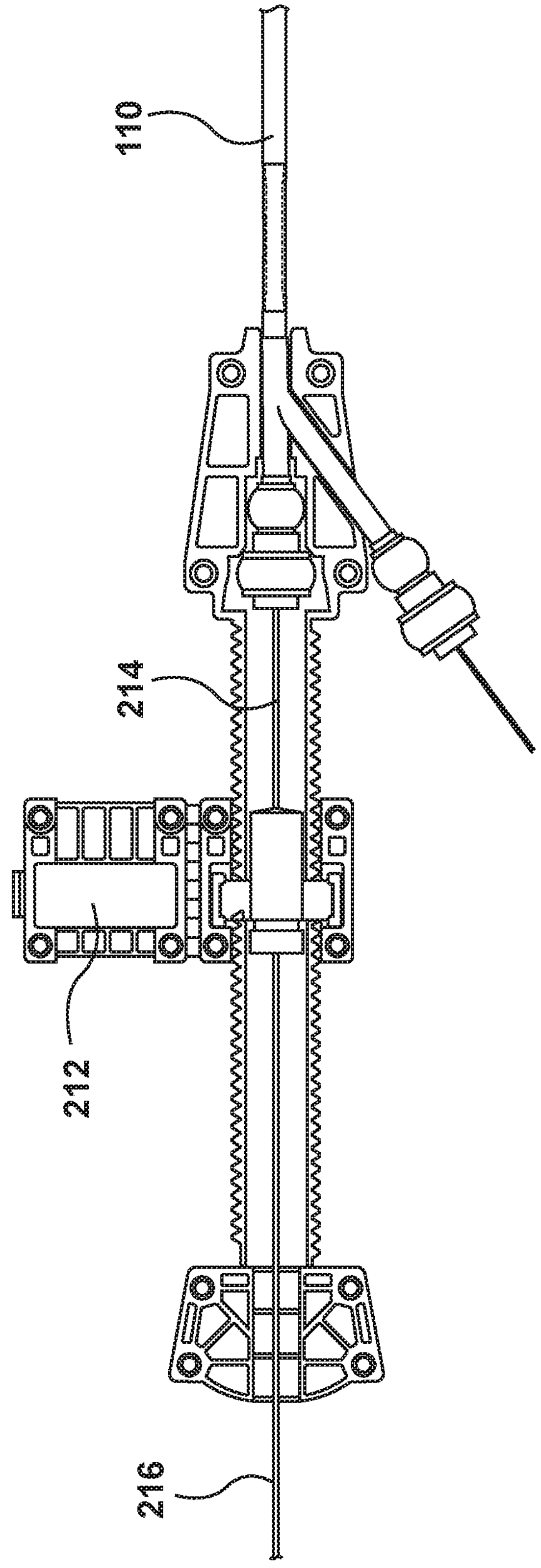

FIG. 17 shows a handle 202 for the outer delivery catheter 102 and a handle 204 for the inner catheter 110. The handle 202 includes actuators 208, 210 to steer the delivery catheter 102. The handle 204 includes an actuator 212 for deploying the electrode assembly 140. FIG. 18 shows a cut-away view of the handle 204, including a hypotube 214 extending proximally from the electrode assembly 140 and an electrical connection 216 for the electrodes of the electrode assembly 140.

Figure 19:
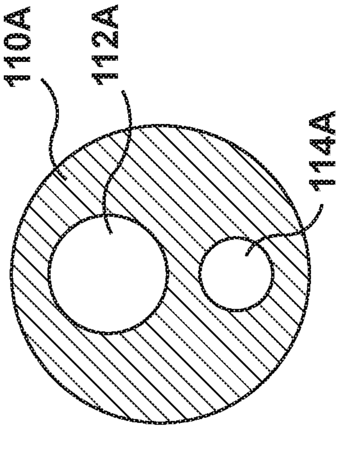

FIG. 19 shows another embodiment of the inner catheter 110A, which is ovalized as compared to the inner catheter 110 shown in FIG. 2. The ovalized design assists in keeping the electrode assembly 140 straight as it exits the first lumen 112A.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components.

What is claimed is:

1. A valve leaflet resection device comprising:

a catheter;

an electrode assembly slidably disposed within the catheter and deployable from the catheter and configured to remove a portion of a leaflet of a heart valve, wherein the electrode assembly comprises a shape set wire including a first arm and a second arm, wherein the first arm and second arm include a straightened configuration wherein the first arm and the second arm are adjacent to each other and a splayed configuration wherein the first arm and the second arm are separated from each other, each of the first arm and the second arm including an electrode configured to resect a portion of the leaflet to be resected in the splayed configuration, wherein the shape set wire is shape set to the splayed configuration;

a leaflet retainer slidably disposed within the catheter and deployable from the catheter, the leaflet retainer configured to grasp a leaflet of a heart valve; and a capture basket configured to capture a resected portion of the leaflet of the heart valve upon retraction of the leaflet retainer.

2. The valve leaflet resection device of claim 1, wherein the capture basket includes a radially compressed configuration and a radially expanded configuration.

3. The valve leaflet resection device of claim 2, wherein the capture basket is a tapered mesh tube having a distal end with a first dimension in the radially expanded configuration transverse to a central longitudinal axis of the catheter and a proximal end with a second dimension in the radially expanded configuration transverse to the central longitudinal axis, wherein the second dimension is smaller than the first dimension.

4. The valve leaflet resection device of claim 1, wherein the capture basket is disposed co-axially around the leaflet retainer.

5. The valve leaflet resection device of claim 1, wherein the capture basket further includes a wire or tube extending proximally to an actuator to translate the capture basked proximally and distally in and out of the catheter.

6. The valve leaflet resection device of claim 1, wherein the capture basket is attached to a distal end of the catheter.

7. The valve leaflet resection device of claim 1, wherein the leaflet retainer comprises a wire including a hook at a distal end thereof, wherein the wire is shape set to form the hook as the wire is distally advanced out of the catheter.

8. The valve leaflet resection device of claim 1, wherein the leaflet retainer comprises a tube and a balloon slidably disposed within the tube, wherein the tube is configured to be advanced adjacent to a first side of the leaflet to be resected, the balloon in an uninflated state is configured to exit the tube and advance through the leaflet to a second side of the leaflet, and wherein the balloon is further configured to be inflated to an inflated state wherein the leaflet is captured between the balloon in the inflated state and the tube.

9. The valve leaflet resection device of claim 1, wherein the leaflet retainer comprises a tube and a wire having a shape set tip slidably disposed within the tube, wherein the tube is configured to be advanced adjacent to a first side of the leaflet to be resected, the wire in a straightened configuration is configured to exit the tube and advance through the leaflet to a second side of the leaflet, and wherein the shape set tip is configured to bend to its shape set to capture the leaflet between the shape set tip and the tube.

10. The valve leaflet resection device of claim 1, wherein the leaflet retainer comprises a proximal balloon and a distal balloon, wherein the proximal balloon and the distal balloon are configured to be advanced adjacent to first side of the leaflet to be resected in an uninflated state, the distal balloon in the uninflated state is configured to exit be advanced through the leaflet to a second side of the leaflet, and wherein the proximal and distal balloons are further configured to be inflated to an inflated state such that the leaflet is captured between the proximal balloon and the distal balloon.

11. The valve leaflet resection device of claim 1, wherein the leaflet retainer comprises a shape set wire configured to form a proximal radial bump and a distal radial bump in a shape set configuration, wherein the shape set wire is configured to be advanced adjacent to first side of the leaflet to be resected in a straightened configuration, the wire in the straightened configuration is configured to exit the tube and advance through the leaflet to a second side of the leaflet, and wherein the wire is configured to return to shape set configuration to capture the leaflet between the proximal radial bump on the first side of the leaflet and the distal radial bump on the second side of the leaflet.

12. The valve leaflet resection device of claim 1, wherein the leaflet retainer includes a shaft having an auger or helical coil at a distal end of the shaft, wherein the shaft is configured to be advanced through the leaflet to be resected such that a first portion of the auger or helical coil is on a first side of the leaflet and a second portion of the auger or helical coil is on a second side of the leaflet to grasp the leaflet.

13. The valve leaflet resection device of claim 1, wherein the leaflet retainer includes a shaft with a proximal retainer and a distal retainer disposed on the shaft, wherein the proximal and distal retainers include a radially compressed configuration when disposed within the catheter, wherein the catheter is configured to the advanced to a first side of the leaflet to be resected, the leaflet retainer is configured to be advanced from the catheter through the leaflet such that the distal retainer is on a second side of the leaflet and the proximal retainer is on the first side of the leaflet, and wherein the distal and proximal retainers are configured to radially expand to a radially expanded configuration when exiting the catheter such that the leaflet is captured between the proximal leaflet and the distal leaflet with each in the radially expanded configuration.

14. A valve leaflet resection device comprising:

a catheter;

an electrode assembly slidably disposed within the catheter and deployable from the catheter and configured to remove a portion of a leaflet of a heart valve;

a leaflet retainer slidably disposed within the catheter and deployable from the catheter, the leaflet retainer configured to grasp a leaflet of a heart valve, the leaflet retainer comprises a wire including a hook at a distal end thereof, wherein the wire is shape set to form the hook as the wire is distally advanced out of the catheter, wherein the leaflet retainer further includes an electrode at the distal end thereof configured to pierce the leaflet to be resected; and a capture basket configured to capture a resected portion of the leaflet of the heart valve upon retraction of the leaflet retainer.

15. The valve leaflet resection device of claim 14, wherein the electrode assembly includes a first arm and a second arm, wherein the first and second arms include a straightened configuration wherein the first and second arm are adjacent to each other and a splayed configuration wherein the first and second arm are separated from each other, each of the first arm and the second arm including an electrode configured to resect a portion of the leaflet to be resected.

16. The valve leaflet resection device of claim 15, wherein the first and second arms are formed of shape memory material and are shape set to the splayed configuration.

17. The valve leaflet resection device of claim 16, further comprising a balloon nested between the first and second arms of the electrode assembly, wherein the balloon is configured to be inflated to separate the first and second arms into the splayed configuration.

18. The valve leaflet resection device of claim 16, further comprising a shaft including an enlarged distal end, wherein the shaft is slidable relative to the electrode assembly, and wherein the shaft is configured to be advanced to drive the enlarged distal end between the first and second arms to splay the first and second arms to the splayed configuration.

19. The valve leaflet resection device of claim 15, further comprising a puncture electrode disposed at a distal end of the electrode assembly with the first and second arms in the straightened configuration.

20. A method of resecting a portion of a leaflet comprising:

advancing a leaflet resection device to a first side of a leaflet to be resected, the leaflet to be resected being a native leaflet or a leaflet of an implanted heart valve prosthesis;

advancing an electrode assembly of the leaflet resection device through the leaflet such that at least a portion of the electrode assembly is disposed on a second side of the leaflet to be resected;

grasping the leaflet to be resected with a leaflet retainer of the leaflet resection device;

activating the electrode assembly to remove a portion of the leaflet to be resected while the leaflet retainer is grasping the portion of the leaflet to be resected; and retracting the leaflet retainer with the portion of the resected leaflet into a leaflet capture basket.

* * * * *